US011123073B2

(12) United States Patent
Zhang et al.

(10) Patent No.: US 11,123,073 B2
(45) Date of Patent: Sep. 21, 2021

(54) ADJUSTABLE ROTATION ASSEMBLY FOR SURGICAL INSTRUMENTS (71) Applicant: Covidien LP, Mansfield, MA (US)

(72) Inventors: Jiangfeng Zhang, Shanghai (CN); Nishant Mehta, Maharashtra (IN); Zhinan Guo, Shanghai (CN)

(73) Assignee: Covidien LP, Mansfield, MA (US)

( * ) Notice: Subject to any disclaimer, the term of this patent is extended or adjusted under 35 U.S.C. 154(b) by 224 days.

(21) Appl. No.: 16/485,462

(22) PCT Filed: Jun. 8, 2017

(86) PCT No.: PCT/CN2017/087521
§ 371 (c)(1),
(2) Date: Aug. 13, 2019

(87) PCT Pub. No.: WO2018/223324
PCT Pub. Date: Dec. 13, 2018

(65) Prior Publication Data
US 2020/0038027 A1 Feb. 6, 2020

(51) Int. Cl.
*A61B 17/072* (2006.01)
*A61B 17/115* (2006.01)
(Continued)

(52) U.S. Cl.
CPC ...... *A61B 17/115* (2013.01); *A61B 17/07207* (2013.01); *A61B 17/068* (2013.01);
(Continued)

(58) Field of Classification Search
CPC ............... A61B 17/068; A61B 17/072; A61B 17/07207; A61B 17/115;
(Continued)

(56) References Cited

U.S. PATENT DOCUMENTS 5,312,023 A * 5/1994 Green ............. A61B 17/07207
227/175.1
5,582,615 A * 12/1996 Foshee ............... A61B 17/2909
606/139
(Continued)

FOREIGN PATENT DOCUMENTS

| CN | 101474088 A | 7/2009 |
| CN | 105358081 A | 2/2016 |

OTHER PUBLICATIONS

International Search Report for PCT/CN2017/087521 date of completion is Feb. 11, 2018 (4 pages).

*Primary Examiner* — Scott A Smith
(74) *Attorney, Agent, or Firm* — Carter, DeLuca & Farrell LLP (57) ABSTRACT

A surgical instrument (10) includes a handle assembly (20), an elongate body portion (50) extending from the handle assembly (20) and defining a longitudinal axis, and a rotation assembly (100) rotatably securing the elongate body portion (50) to the handle assembly (20). The rotation assembly (100) includes a sleeve member (110) and a rotation knob (120) supported about the sleeve member (110). The rotation knob (120) is movable relative to the sleeve member (110) and the handle assembly (20) along the longitudinal axis.

18 Claims, 6 Drawing Sheets

(51) Int. Cl.
*A61B 17/00* (2006.01)
*A61B 17/29* (2006.01)
*A61B 17/068* (2006.01)

(52) U.S. Cl.
CPC ............... *A61B 2017/0042* (2013.01); *A61B 2017/00464* (2013.01); *A61B 2017/00473* (2013.01); *A61B 2017/00477* (2013.01); *A61B 2017/07214* (2013.01); *A61B 2017/292* (2013.01); *A61B 2017/2929* (2013.01)

(58) Field of Classification Search
CPC ........... A61B 2017/00473; A61B 2017/00477; A61B 2017/07214; A61B 2017/292; A61B 2017/2923; A61B 2017/2929; A61B 2017/042
USPC .............. 227/19, 175.1, 176.1, 178.1, 180.1; 606/1, 139, 153, 219
See application file for complete search history.

(56) References Cited

U.S. PATENT DOCUMENTS

| | | | |
|---|---|---|---|
| 5,662,662 A * | 9/1997 | Bishop | A61B 17/0684 227/175.1 |
| 5,782,844 A * | 7/1998 | Yoon | A61B 17/064 606/139 |
| 5,910,105 A * | 6/1999 | Swain | A61B 1/018 600/131 |
| 6,032,849 A | 3/2000 | Mastri et al. | |
| 6,099,537 A * | 8/2000 | Sugai | A61B 17/0684 606/143 |
| 6,942,674 B2 * | 9/2005 | Belef | A61B 17/0057 606/139 |
| 7,000,819 B2 * | 2/2006 | Swayze | A61B 17/07207 227/176.1 |
| 9,028,495 B2 * | 5/2015 | Mueller | A61B 17/29 606/52 |
| 9,351,728 B2 | 5/2016 | Sniffin et al. | |
| 9,433,400 B2 | 9/2016 | Miller | |
| 9,783,329 B2 | 10/2017 | Sniffin et al. | |
| 2006/0161190 A1 | 7/2006 | Gadberry et al. | |
| 2009/0069842 A1 * | 3/2009 | Lee | A61B 50/30 606/205 |
| 2009/0236395 A1 | 9/2009 | Scirica | |
| 2010/0030262 A1 * | 2/2010 | McLean | A61B 17/0401 606/232 |
| 2010/0298784 A1 | 11/2010 | Miller | |
| 2011/0204120 A1 * | 8/2011 | Crainich | A61B 17/07207 227/180.1 |
| 2014/0025067 A1 | 1/2014 | Kerr et al. | |
| 2015/0005748 A1 | 1/2015 | Sniffin et al. | |
| 2015/0005788 A1 | 1/2015 | Sniffin et al. | |
| 2016/0367288 A1 | 12/2016 | Miller | |

\* cited by examiner

ADJUSTABLE ROTATION ASSEMBLY FOR SURGICAL INSTRUMENTS

CROSS-REFERENCE TO RELATED APPLICATIONS

This application is a National Stage Application of PCT/CN2017/087521 under 35USC § 371 (a), the disclosure of the above-identified application is hereby incorporated by reference in its entirety.

BACKGROUND

Technical Field

The present disclosure relates to handle assemblies for surgical instruments. More particularly, the present disclosure relates to rotation assemblies for the handle assemblies of the surgical instruments.

Background of Related Art

Surgical instruments for performing surgical procedures typically include a handle assembly for actuating various end effectors. The end effectors may include stapler assemblies, jaw members, vessel sealers, retractors, etc. Generally, the end effector is disposed on an elongate body portion of the surgical instrument that extends from the handle assembly. In many instances, the elongate body portion of the surgical instrument is rotatably supported by the handle assembly to permit rotation of the end effector along a longitudinal axis of the elongate body portion. A rotation knob is typically supported in a fixed longitudinal position on a proximal portion of the elongate body portion, adjacent the handle assembly. In the fixed position, the rotation knob may interfere with the comfort of the user and/or the operation of the surgical instrument.

Therefore, it would be beneficial to have a surgical instrument with a rotation assembly having an adjustable rotation knob.

SUMMARY

A surgical instrument having an adjustable rotation knob is provided. The surgical instrument includes a handle assembly, an elongate body portion extending from the handle assembly and defining a longitudinal axis, and a rotation assembly rotatably securing the elongate body portion to the handle assembly. The rotation assembly includes a sleeve member and a rotation knob supported about the sleeve member. The rotation knob is movable relative to the sleeve member and the handle assembly along the longitudinal axis.

In embodiments, the rotation knob may be rotationally fixed relative to the sleeve member. The sleeve member may include a spine and the rotation knob may define a slot for receiving the spine. Rotation of the rotation knob about the longitudinal axis causes rotation of the sleeve member about the longitudinal axis. The rotation knob may define a recess for receiving a compression spring and a ball member. The ball member may be biased into engagement with the sleeve member by the compression spring. The sleeve member may define a plurality of notches with each notch of the plurality of notches being configured for receipt of the ball member.

In embodiments, a distal portion is configured to support an end effector. The end effector may include a stapler reload. The handle assembly may include a stationary handle and a movable handle pivotally secured relative to the stationary handle. The elongate body portion may include an outer sleeve and a drive shaft. The rotation assembly may include a fastener nut for securing the sleeve member to the handle assembly. The rotation assembly may include a fastener knob for securing the elongate body portion to the sleeve member.

Also provided is a rotation assembly for securing an elongate body portion to a handle assembly. The rotation assembly includes a sleeve member defining a longitudinal axis and configured to be rotatably supported on a handle assembly, and a rotation knob slidably disposed about the sleeve member the sleeve member including a distal end configured to support an elongate body portion. The rotation knob is movable relative to the sleeve member along the longitudinal axis.

In embodiments, the rotation knob is rotationally fixed relative to the sleeve member. The sleeve member may include a spine and the rotation knob may define a slot for receiving the spine. Rotation of the rotation knob about the longitudinal axis may cause rotation of the sleeve member about the longitudinal axis. The rotation knob may define a recess for receiving a compression spring and a ball member. The ball member may be biased into engagement with the sleeve member by the compression spring. The sleeve member may define a plurality of notches with each notch of the plurality of notches being configured for receipt of the ball member.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiment(s) given below, serve to explain the principles of the disclosure, wherein.

DETAILED DESCRIPTION

Embodiments of the presently disclosed hand instrument with adjustable rotation assembly will now be described in detail with reference to the drawings in which like reference numerals designate identical or corresponding elements in each of the several views. As is common in the art, the term "proximal" refers to that part or component closer to the user or operator, i.e. surgeon or clinician, while the term "distal" refers to that part or component further away from the user.

Although the embodiments of the rotation knob assembly of the present disclosure will be shown and described with regards to a manually actuated handle assembly, it is envisioned that the aspects of the present disclosure may be modified for use with handle assemblies having different configurations, e.g., powered, pistol grip, pencil grip.

Figure 1:
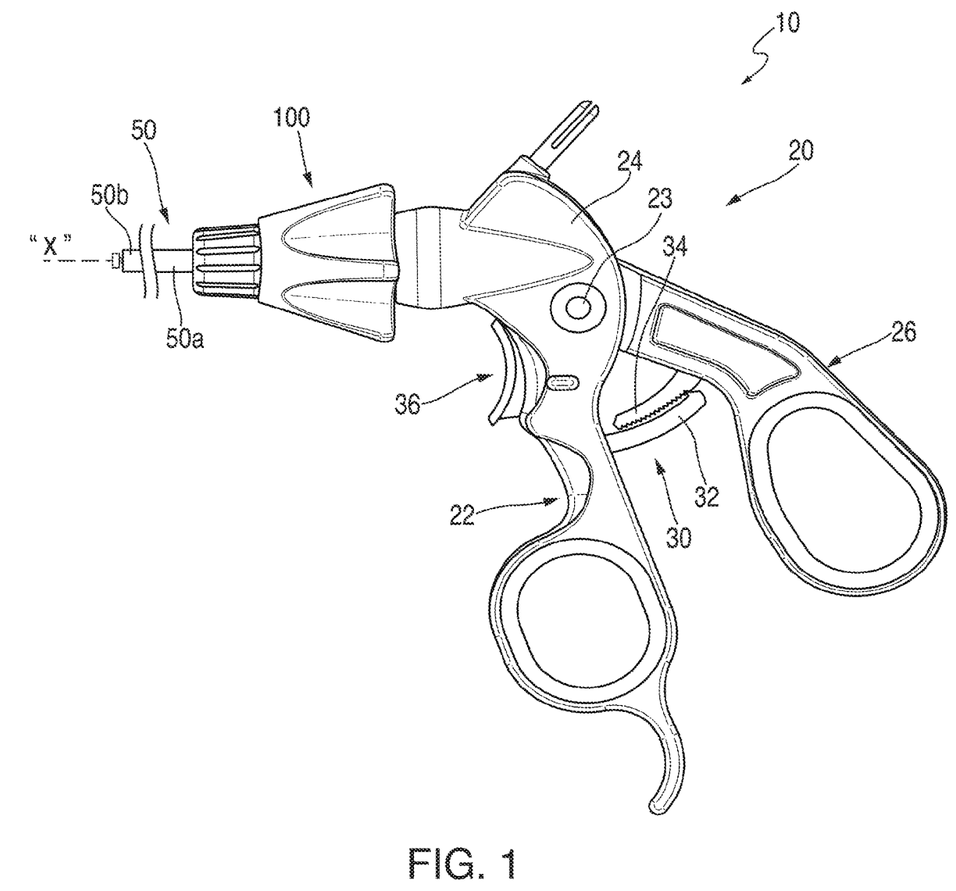
FIG. 1 is a perspective view of a surgical instrument including a rotation assembly according to an embodiment of the present disclosure, with the rotation knob in a proximal position.
Figure 8:
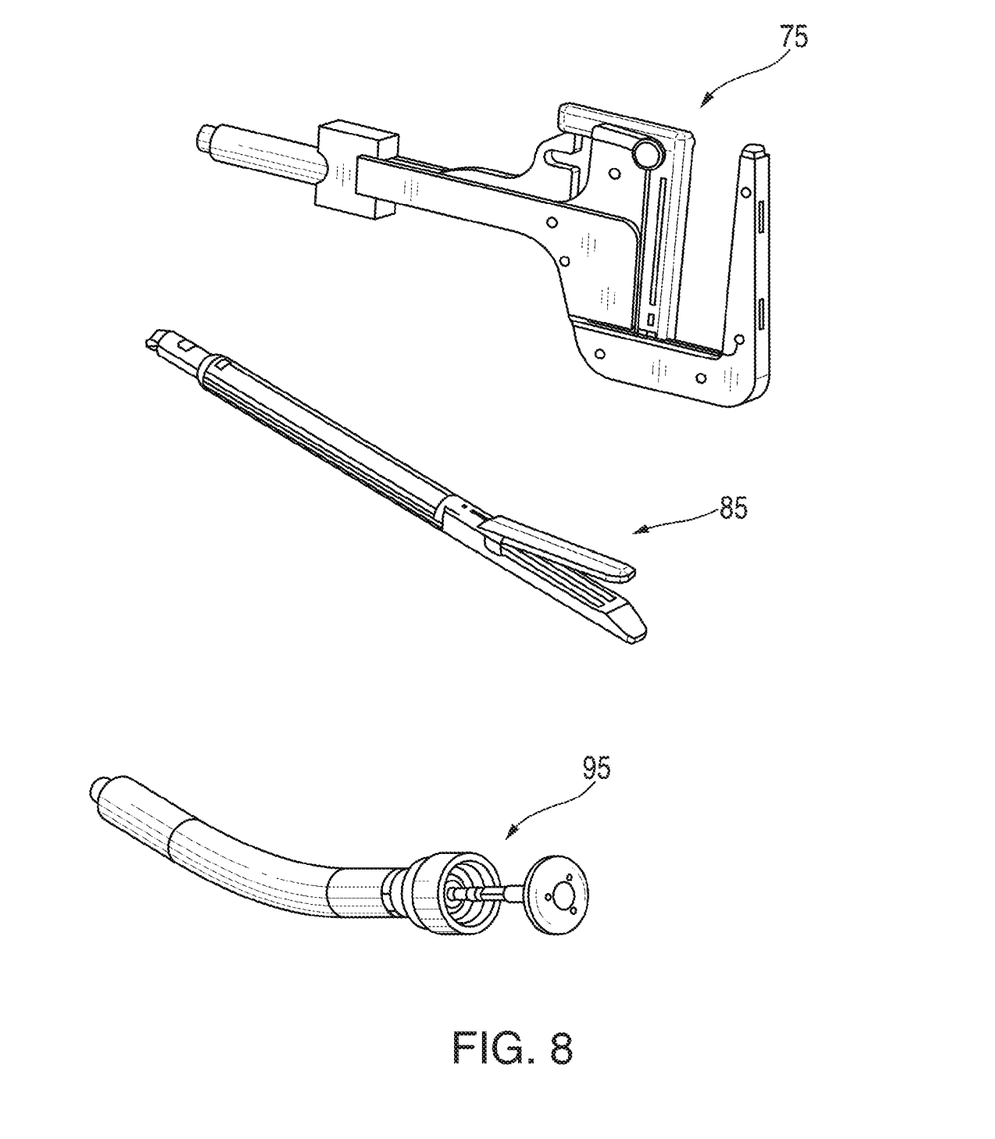
FIG. 8 is a perspective view of various stapling assembly reloads.

With reference initially to FIG. 1, a surgical instrument according to an embodiment of the present disclosure is shown generally as surgical instrument 10. The surgical instrument 10 includes a handle assembly 20 and an elongate body portion 50 extending from the handle assembly 20. As will be described in further detail below, the elongate body portion 50 of the surgical instrument 10 is secured to the handle assembly 20 by a rotation assembly 100. The rotation assembly 100 is configured to effect rotation of the elongate body portion 50 along a longitudinal axis "x" of the elongate body portion 50 to thereby rotate an end effector (see, for example, FIG. 8) disposed on a distal end 50b of the elongate body portion 50 about the longitudinal axis "x" of the elongate body portion 50.

The surgical instrument 10 will only be described to the extent necessary to fully disclose the aspects of the present disclosure. In embodiments, the surgical instrument 10 may include end effectors of various configurations, including but not limited to stapler assemblies (see, for example, FIG. 8—a transverse anastomosis (TA) reload 75, an endo-gastrointestinal anastomosis (endo-GIA) reload 85, and an end-to-end anastomosis (EEA) reload 95), jaw members, vessel sealers, and retractors. The various end effectors may be integrally formed with the elongate body portion 50 the surgical instrument 10, or, as shown, may be configured for releasable connection from the surgical instrument 10. The aspects of the present disclosure may also be modified for use with adapter assemblies (not shown) configured to connect the end effectors to a handle assembly (not shown).

The handle assembly 20 of the surgical instrument 10 includes a stationary handle 22 extending from a base portion 24 and a movable handle 26 pivotally secured to the base portion 24 by a pivot pin 23. Although shown including the pivot pin 23, either or both of the base portion 24 and the movable handle 26 may include a pivot member for pivotally securing the moveable handle 26 relative to the stationary handle 22.

The handle assembly 20 of the surgical instrument 10 further includes a ratchet assembly 30 for maintaining the position of the movable handle 26 relative to the stationary handle 22 during actuation of the surgical instrument 10. The ratchet assembly 30 includes a first ratchet member 32 extending from the stationary handle 22 towards the movable handle 26, and a second ratchet member 34 extending from the movable handle 26 towards the stationary handle 22. In embodiments, the first ratchet member 32 engages the second ratchet member 34 in an interlocking manner as the movable handle 26 is moved towards the stationary handle 22, i.e., during actuation of the surgical instrument 10, to lock the movable handle 26 in position relative to the stationary handle 22 thereby fixing the end effector (not shown) in a given condition.

The handle assembly 20 of the surgical instrument 10 may further include a trigger mechanism 36 configured to prevent incidental actuation of the handle assembly 20 during handling and prior to desired actuation. More particularly, the trigger mechanism 36 of the handle assembly 20 fixes the movable handle 26 relative to the stationary handle 22 until the trigger member 36 is pressed.

Figure 2:
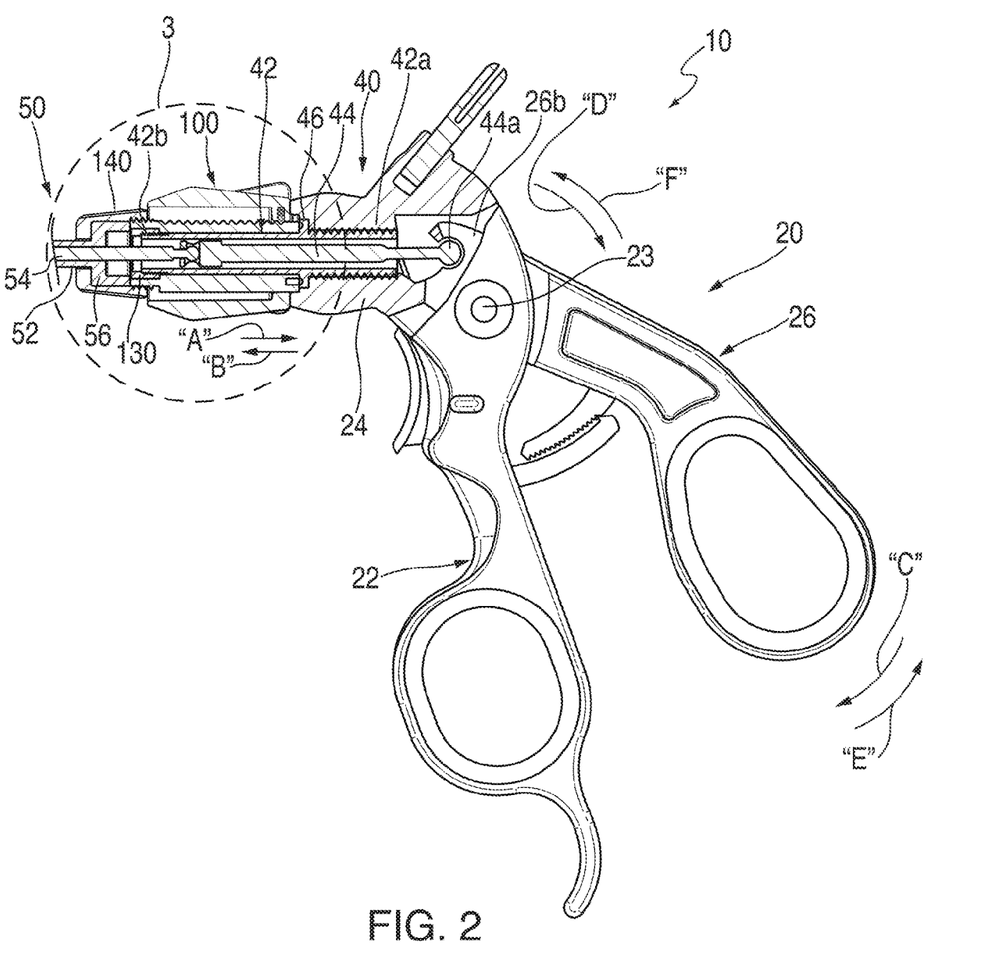
FIG. 2 is a partial cross-sectional view of the surgical instrument shown in FIG. 1.

With particular reference to FIG. 2, the handle assembly 20 of the surgical instrument 10 includes a drive assembly 40 operably disposed within the base portion 24 of the handle assembly 20. The drive assembly 40 includes a fixation tube 42 secured to the base portion 24, and a drive member 44 extending through the fixation tube 42. The fixation tube 42 of the drive assembly 40 includes externally threaded proximal and distal ends 42a, 42b, respectively. The threaded proximal portion 42a of the fixation tube 42 engages the base portion 24 of the handle assembly 20 in a threaded manner. The threaded distal portion 42b of the fixation tube 42 engages a fastener nut 130 of the rotation assembly 100 in a threaded manner Although shown as a thread connection between the base portion 24 of the handle assembly 20 and the proximal portion 42a of the fixation tube 42 and between the distal portion 42b of the fixation tube 42 and the fastener nut 130 of the rotation assembly 100, it is envisioned that either or both of these connections may instead include, a press-fit connection, a bayonet coupling, or the components may be welded, adhered, or other suitably secured to one another. In embodiment, the connections between the base portion 24 of the handle assembly 20 and the proximal portion 42a of the fixation tube 42 and between the distal portion 42b of the fixation tube 42 and the fastener nut 130 of the rotation assembly 100 are releasable.

A flange 46 is disposed between the proximal and distal portions 42a, 42b of the fixation tube 42. The flange 46 provides a stop to prevent over-insertion of the fixation tube 42 within the base portion 24 of the handle assembly 24. The flange 46 also provides a stop to prevent over-insertion of the sleeve member 110 of the rotation assembly 100 about the fixation tube 42.

A proximal portion 44a of the drive member 44 of the drive assembly 40 of the handle assembly 20 is pivotally secured to a distal portion 26b of the moveable handle 26. In embodiments, and as shown, the drive assembly 40 of the handle assembly 20 is configured move a drive rod 54 of the elongate body portion 50 of the surgical instrument 10 in a proximal direction, i.e., retract, as indicated by arrow "A" in FIG. 2, when the moveable handle 26 is moved towards the stationary handle 22, i.e., in a clockwise direction, as indicated by arrow "C" in FIG. 2. Conversely, movement of the moveable handle 26 away from the stationary handle 22, i.e., in a counter-clockwise direction, as indicated by arrow "E" in FIG. 2, moves the drive rod 54 in a distal direction, i.e., advances, as indicated by arrow "B" in FIG. 2. The configuration of the end effector determines which of the retracting or advancing movements of the drive rod 54 actuates the end effector.

With continued reference to FIG. 2, as the movable handle 26 of the handle assembly 20 is pivoted towards the station handle 22 of the handle assembly 20, in a clockwise direction, as indicated by arrow "C", the distal portion 26b of the moveable handle 26 pivots about the pivot pin 23, in the same clockwise direction, as indicated by arrow "D". The clockwise movement of the distal portion 26b of the moveable handle 26 moves the drive member 44 in the proximal direction, as indicated by arrow "A". Conversely, as the movable handle 26 of the handle assembly 20 is pivoted away from the station handle 22 of the handle assembly 20, as indicated by arrow "E", in a counter-clockwise direction, the distal portion 26b of the moveable handle 26 pivots about the pivot pin 23, as indicated by arrow "F", in the same counter-clockwise direction. The counter-clockwise movement of the distal portion 26b of the moveable handle 26 moves the drive member 44 in the distal direction, as indicated by arrow "B".

Figure 3:
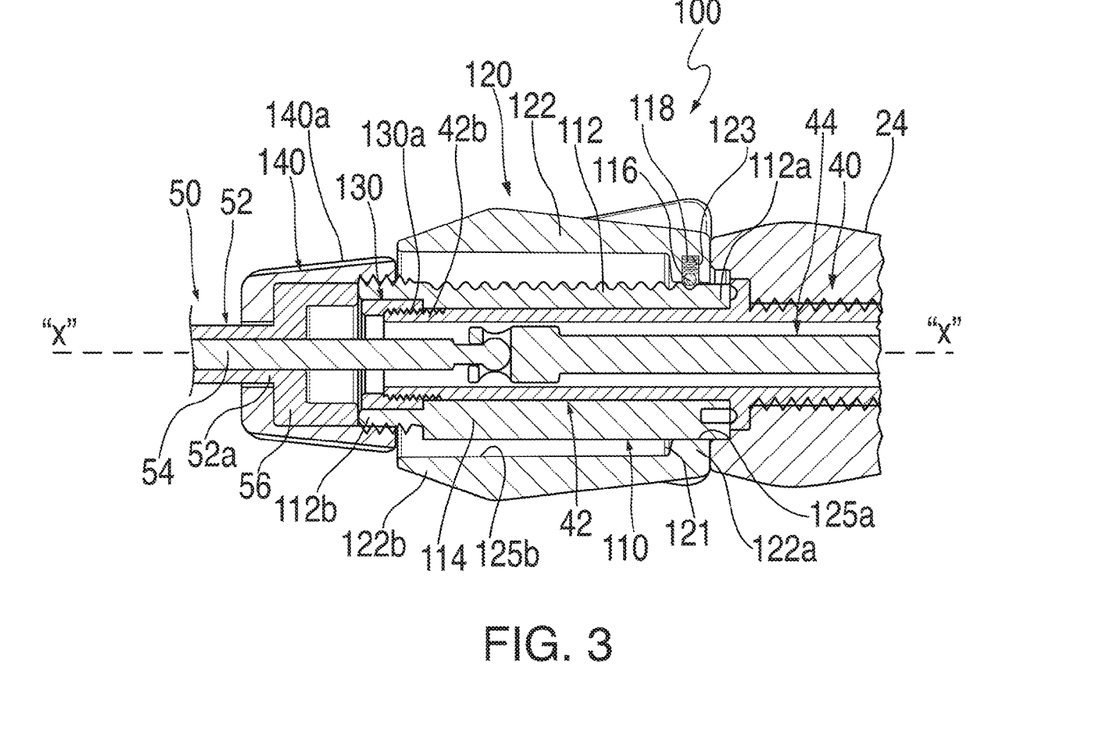
FIG. 3 is an enlarged view of the indicated area of detail shown in FIG. 2.

With additional reference to FIG. 3, as noted above, the elongated body portion 50 of the surgical instrument 10 extends from the handle assembly 20 and is rotatably secured to the handle assembly 20 by the rotation assembly 100. The elongate body portion 50 includes an outer sleeve 52 and the drive rod 54 slidably disposed within the outer sleeve 52. The distal end 50b of the elongate body portion 50 is configured to support an end effector (see, for example, FIG. 8). The end effector may be releasably secured to the distal end 50b of the elongate body portion 50, e.g., replaceable loading unit, or may be secured directly to or integrally formed with the elongate body portion 50.

A proximal portion 52a of the outer tube 52 of the elongate body portion 50 includes a flange 56 configured to facilitate attachment of the outer tube 52 to a sleeve member 110 of the rotation assembly 100. More particularly, and as will be described in further detail below, the flange 56 of the outer tube 52 abuts the distal portion 42b of the sleeve member 110 of the rotation assembly 100 and is secured to the sleeve member 110 by a fastener knob 140 of the rotation assembly 100.

With continued reference to FIG. 3, the rotation assembly 100 of the surgical instrument 10 includes the sleeve member 110, a rotation knob 120 slidably disposed about the sleeve member 110, the fastener nut 130 for securing the sleeve member 110 to the fixation tube 42 of the drive assembly 40 of the handle assembly 20, and the fastener knob 140 for securing the elongate body portion 50 of the surgical instrument 10 to the sleeve member 110.

Figure 4:
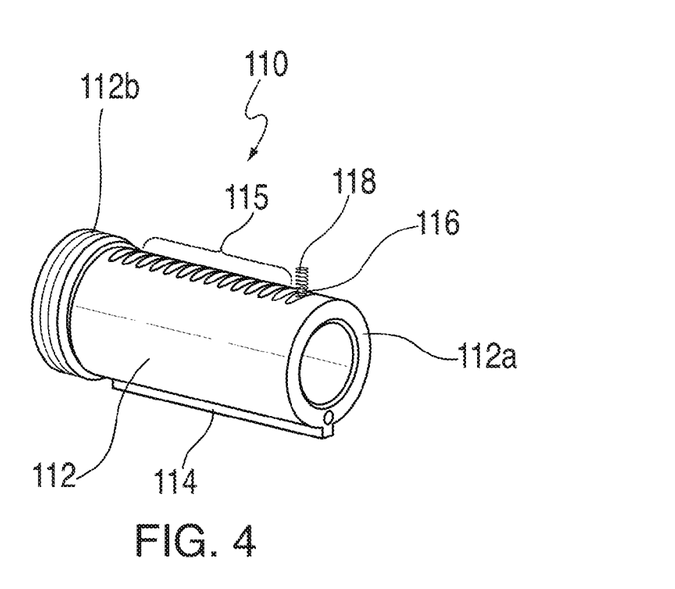
FIG. 4 is a perspective view of a sleeve member of the rotation assembly shown in FIG. 1.

With additional reference to FIG. 4, the sleeve member 110 of the rotation assembly 100 of the surgical instrument 10 includes a tubular body 112 sized to be received about the fixation tube 42 of the drive assembly 40 of the handle assembly 20, and within the rotation knob 120. The tubular body 112 includes a proximal portion 112a and an externally threaded distal portion 112b. The proximal portion 112a of the tubular body 112 is configured to abut the flange 56 of the fixation tube 42 of the drive assembly 40 of the handle assembly 20. The externally threaded distal portion 112b of the tubular body 112 is configured to engage a threaded proximal portion 140a of fastener knob 140. The threaded distal portion 112b of the tubular body 112 further defines a cutout 113 dimensioned to receive the fastener nut 130 of the rotation assembly 130.

Figure 5:
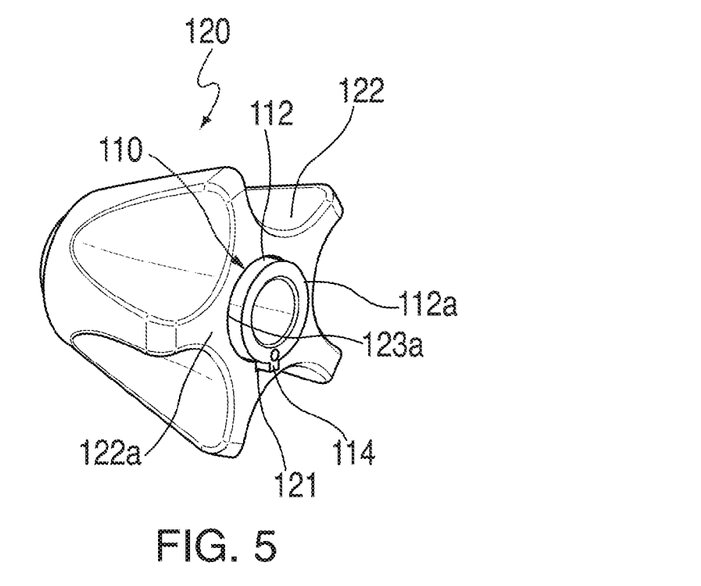
FIG. 5 is a perspective view of a rotation knob and the sleeve member of the rotation assembly shown in FIG. 1.

With reference still to FIG. 4, the tubular body 112 of the sleeve member 110 of the rotation assembly 100 includes a spine 114 extending along a length thereof. The spine 114 on the tubular body 112 is configured to be received within a slot 121 (FIG. 5) of the rotation knob 120 (FIG. 5). Although shown as a spine 114, it is envisioned that the sleeve member 110 may instead include a groove (not shown) for receiving a tab(s) or spine(s) (not shown) formed on the rotation knob 120.

The tubular body 112 of the sleeve member 110 of the rotation assembly 100 defines a plurality of notches 115 extending along an outer surface of the tubular body 112. The notches 115 are configured to engage a ball member 116. The ball member 116 is received within a recess 123 (FIG. 3) of the rotation knob 120 and is biased radially outward by a compression spring 118.

With additional reference to FIG. 5, the rotation knob 120 of the rotation assembly 100 includes a handle member 122 configured to be engaged by a user and to receive the sleeve member 110 of the rotation assembly 100. The handle member 122 may be scalloped, as shown, and/or may be knurled (not shown) or otherwise configured to facilitate engagement by a user. The body member 122 may include a coating (not shown) of slip resistant material.

Figure 6:
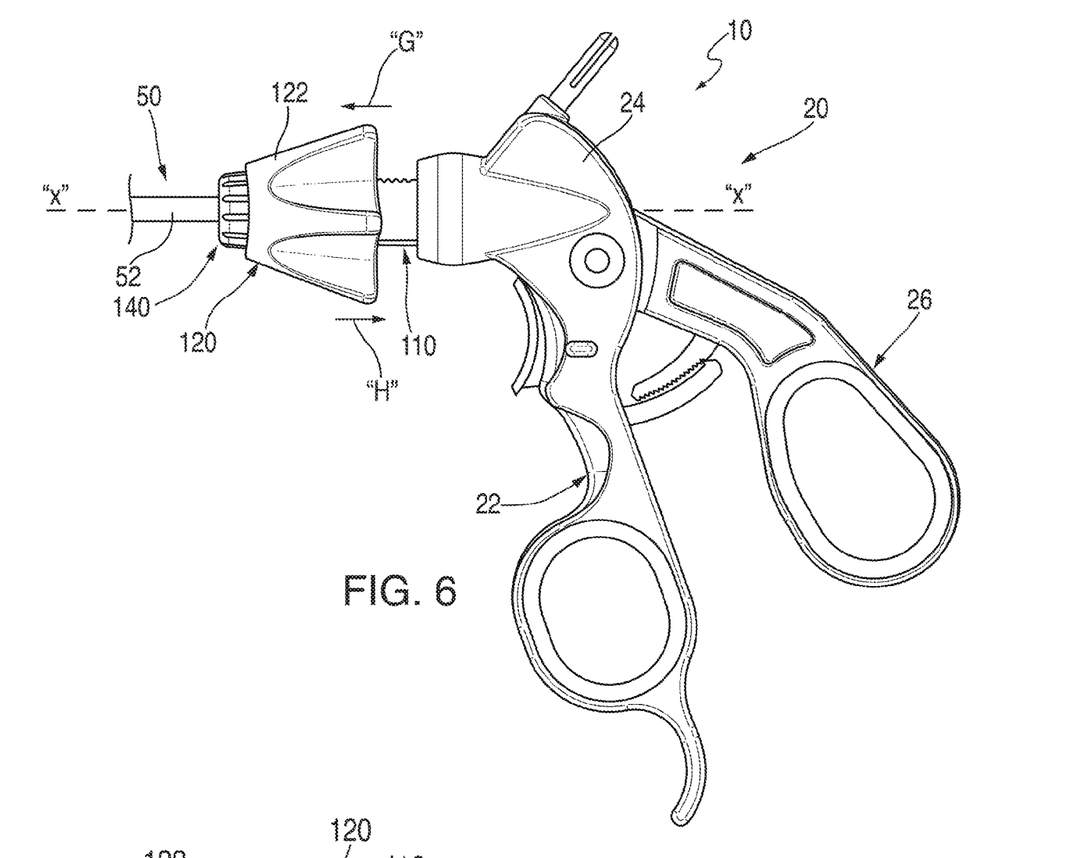
FIG. 6 is a perspective view of the surgical instrument shown in FIG. 1, with the rotation knob of the rotation assembly in an intermediate position.
Figure 7:
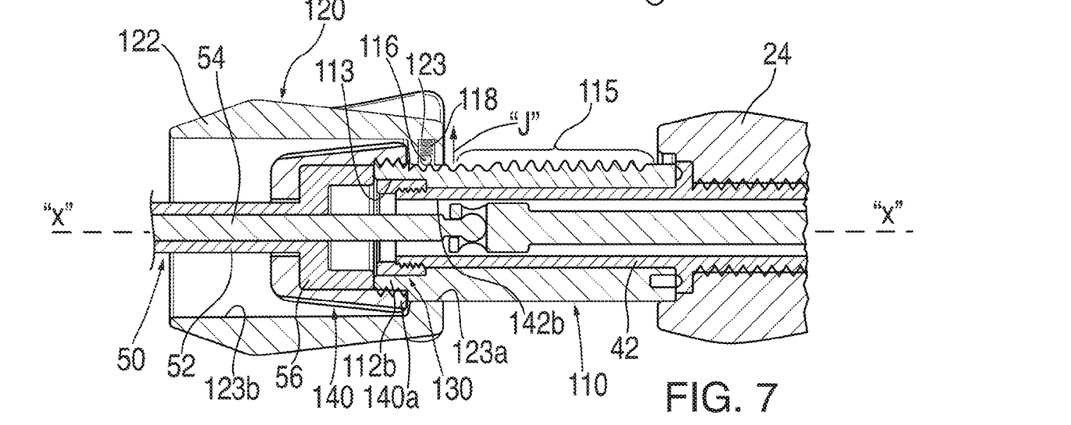
FIG. 7 is a cross-sectional side view of the rotation assembly shown in FIG. 4, with the rotation knob of the rotation assembly in distal position.

As best seen in FIG. 7, the handle member 122 of the rotation knob 120 of the rotation assembly 100 includes a proximal portion 122a defining a first cylindrical opening 123 dimensioned to receive the sleeve member 110 therethrough and a distal portion 122b defining a second cylindrical opening 125 dimensioned to receive the fastener knob 140 therein. The rotation knob 120 is configured to be moved along the longitudinal axis "x" relative to the sleeve member 110 from a proximal position (FIG. 3), to a distal position (FIG. 7), and intermediate positions therebetween (see, for example, FIG. 6). The intermediate positions correspond with the plurality of notches 115 of the tubular body 112 of the sleeve member 110. The number and spacing of the plurality of notches 115 determines the location of the intermediate positions.

As noted above, the rotation knob 120 of the rotation assembly 100 defines the slot 121 for receiving the spine 114 of the sleeve member 110, and the recess 123 for receiving the ball member 116 and the compression member 118. When the rotation knob 120 is received about the tubular body 112 of the sleeve member 110 such that the spine 114 of the sleeve member 110 is received within the slot 121 of the rotation knob 120, the rotation knob 120 is rotationally fixed relative to the sleeve member 110. In this manner, the sleeve member 110 will rotate about the longitudinal axis "x" of the elongate body portion 50 relative to the handle assembly 20 as the rotation knob 120 is rotated about the longitudinal axis "x" relative to the handle assembly 20.

With continued reference to FIG. 3, the fastener nut 130 of the rotation assembly 100 secures the sleeve member 110 of the rotation assembly 100 about the fixation tube 42 of the drive assembly 40 of the handle assembly 20. More particularly, the fastener nut 130 is received within the cutout 113 in the distal portion 112b of the tubular body 112 of the sleeve member 110. A threaded proximal portion 130a of the fastener nut 130 engages the threaded distal portion 42b of the fixation tube 42 of the drive assembly 40. The fastener nut 130 fixes the sleeve member 110 from longitudinal movement relative to the fixation tube 42 of the drive assembly 40 while permitting rotation of the sleeve member 110 about the longitudinal axis "x".

With reference still to FIG. 3, as noted above, the fastener knob 140 of the rotation assembly 100 secures the outer sleeve 52 of the elongate body portion 50 of the surgical instrument 10 to the sleeve member 110 of the rotation assembly 100. More particularly, the fastener knob 140 is received over the flange 56 of the outer sleeve 52 of the elongate body portion 50, and the internally threaded proximal portion 140a of the fastener knob 140 engages the externally threaded distal portion 112b of the tubular body 112 of the sleeve member 110 of the rotation assembly 100. By securing the outer sleeve 52 of the elongate body portion 50 to the sleeve member 110 of the rotation assembly 100, the fastener knob 140 rotationally fixes the outer sleeve 52 to the sleeve member 110. In this manner, rotation of the sleeve member 110 causes rotation of the outer sleeve 52 of the elongate body portion 50.

With reference now to FIGS. 6 and 7, the rotation assembly 100 of the surgical instrument 10 is configured such that the position of the rotation knob 120 of the rotation assembly 100 relative to the base portion 24 of the handle assembly 20 may be adjusted at any time prior to, during or subsequent a surgical procedure by the user of the surgical instrument 10. In this manner, prior to using the surgical instrument 10, the surgeon may engage the rotation knob 120 of the rotation assembly 100 and slide the rotation knob 120 along the longitudinal axis "x" of the elongate body portion 50 relative to the handle assembly 20, as indicated by arrows "G" and "H", to find a comfortable and/or more suitable longitudinal position for the rotation knob 120 relative to the handle assembly 20. In addition, at any time during the use of the surgical instrument 10, the user may adjust the position of the rotation knob 120 relative to the handle assembly 20 by engaging the rotation knob 120 and sliding the rotation knob 120 along the longitudinal axis "x" of the elongate body portion 50 relative to the handle assembly 20.

With particular reference to FIG. 7, as noted above, the rotation knob 120 of the rotation assembly 100 of the surgical instrument 10 is maintained relative to the sleeve member 110 of the rotation assembly 100 through engagement of the ball member 116 of the rotation assembly 100 with the sleeve member 110. More particularly, the compression spring 118 biases the ball member 116 radially inwardly into engagement with the sleeve member 110. Receipt of the ball member 116 in one of the plurality of notches 115 of the sleeve member 110 longitudinally fixes the rotation knob 120 relative to the handle assembly 20.

When the rotation knob 120 of the rotation assembly 100 of the surgical instrument 10 (FIG. 6) is engaged by the user, and a force is applied to the rotation knob 120 in a direction parallel to the longitudinal axis "x", the ball member 116 is forced against the bias of the compression spring 118, in the direction indicated by arrow "J" in FIG. 7, into recess 123 in the proximal portion 120a of the rotation knob 120, thereby permitting longitudinal movement of the rotation knob 120 relative to the sleeve member 110. Once a desired longitudinal position of the rotation knob 120 is achieved, the bias provided by the compression spring 118 against the ball member 116 returns the ball member 116 into one of the plurality of notches 115, thereby longitudinally fixing the position of the rotation assembly 120 relative to the handle assembly 20 until such a time that the user desires to reposition the rotation knob 120.

Persons skilled in the art will understand that the devices and methods specifically described herein and illustrated in the accompanying drawings are non-limiting exemplary embodiments. The features illustrated or described in connection with one exemplary embodiment may be combined with the features of other embodiments. Such modifications and variations are intended to be included within the scope of the present disclosure. As well, one skilled in the art will appreciate further features and advantages of the present disclosure based on the above-described embodiments. Accordingly, the present disclosure is not to be limited by what has been particularly shown and described, except as indicated by the appended claims.

The invention claimed is:

1. A surgical instrument comprising
a handle assembly;
an elongate body portion extending from the handle assembly and defining a longitudinal axis; and
a rotation assembly rotatably securing the elongate body portion to the handle assembly, the rotation assembly including a sleeve member and a rotation knob supported about the sleeve member, wherein the rotation knob is movable relative to the sleeve member and the handle assembly along the longitudinal axis.

2. The surgical instrument of claim 1, wherein the rotation knob is rotationally fixed relative to the sleeve member.

3. The surgical instrument of claim 2, wherein the sleeve member includes a spine and the rotation knob defines a slot for receiving the spine.

4. The surgical instrument of claim 1, wherein rotation of the rotation knob about the longitudinal axis causes rotation of the sleeve member about the longitudinal axis.

5. The surgical instrument of claim 1, wherein the rotation knob defines a recess for receiving a compression spring and a ball member, the ball member being biased into engagement with the sleeve member by the compression spring.

6. The surgical instrument of claim 5, wherein the sleeve member defines a plurality of notches, each notch of the plurality of notches being configured for receipt of the ball member.

7. The surgical instrument of claim 1, wherein a distal portion is configured to support an end effector.

8. The surgical instrument of claim 7, wherein the end effector includes a stapler reload.

9. The surgical instrument of claim 1, wherein the handle assembly includes a stationary handle and a movable handle pivotally secured relative to the stationary handle.

10. The surgical instrument of claim 1, wherein the elongate body portion includes an outer sleeve and a drive shaft.

11. The surgical instrument of claim 1, wherein the rotation assembly includes a fastener nut for securing the sleeve member to the handle assembly.

12. The surgical instrument of claim 1, wherein the rotation assembly includes a fastener knob for securing the elongate body portion to the sleeve member.

13. A rotation assembly for securing an elongate body portion to a handle assembly, the rotation assembly comprising:
a sleeve member defining a longitudinal axis and configured to be rotatably supported by a handle assembly, the sleeve member including a distal end configured to support an elongate body portion; and
a rotation knob slidably disposed about the sleeve member, wherein the rotation knob is movable relative to the sleeve member along the longitudinal axis.

14. The rotation assembly of claim 13, wherein the rotation knob is rotationally fixed relative to the sleeve member.

15. The rotation assembly of claim 14, wherein the sleeve member includes a spine and the rotation knob defines a slot for receiving the spine.

16. The rotation assembly of claim 13, wherein rotation of the rotation knob about the longitudinal axis causes rotation of the sleeve member about the longitudinal axis.

17. The rotation assembly of claim 13, wherein the rotation knob defines a recess for receiving a compression spring and a ball member, the ball member being biased into engagement with the sleeve member by the compression spring.

18. The rotation assembly of claim 17, wherein the sleeve member defines a plurality of notches, each notch of the plurality of notches being configured for receipt of the ball member.

* * * * *